(12) United States Patent
Regni, Jr.

(10) Patent No.: US 7,937,140 B2
(45) Date of Patent: May 3, 2011

(54) DETECTION AND DIAGNOSTIC SYSTEM AND METHOD

(76) Inventor: Gerald J. Regni, Jr., Philadelphia, PA (US)

( * ) Notice: Subject to any disclaimer, the term of this patent is extended or adjusted under 35 U.S.C. 154(b) by 0 days.

(21) Appl. No.: 11/811,795

(22) Filed: Jun. 12, 2007

(65) Prior Publication Data

US 2007/0287913 A1    Dec. 13, 2007

Related U.S. Application Data

(63) Continuation-in-part of application No. 11/451,227, filed on Jun. 12, 2006.

(51) Int. Cl.
*A61B 5/05* (2006.01)
(52) U.S. Cl. ........................................ 600/547; 600/407
(58) Field of Classification Search .................. 600/407, 600/373, 437, 477, 547
See application file for complete search history.

(56) References Cited

U.S. PATENT DOCUMENTS

| 5,038,787 | A | * | 8/1991 | Antich et al. | 600/437 |
|---|---|---|---|---|---|
| 5,305,748 | A | * | 4/1994 | Wilk | 600/407 |
| 5,553,610 | A | * | 9/1996 | Lodder | 600/310 |
| 5,800,350 | A | * | 9/1998 | Coppleson et al. | 600/372 |
| 6,002,958 | A | * | 12/1999 | Godik | 600/407 |
| 6,122,537 | A | * | 9/2000 | Schmidt | 600/407 |
| 6,336,045 | B1 | * | 1/2002 | Brooks | 600/547 |
| 6,364,849 | B1 | * | 4/2002 | Wilcox | 600/587 |
| 2005/0065426 | A1 | * | 3/2005 | Porat et al. | 600/407 |
| 2005/0197555 | A1 | * | 9/2005 | Mouradian et al. | 600/365 |
| 2007/0287890 | A1 | * | 12/2007 | Regni | 600/300 |
| 2007/0287913 | A1 | * | 12/2007 | Regni | 600/439 |

* cited by examiner

*Primary Examiner* — Long V Le
*Assistant Examiner* — Saurel J Selkin
(74) *Attorney, Agent, or Firm* — Volpe and Koenig, P.C.

(57) ABSTRACT

A method and apparatus for detecting the presence of substances, compositions, constituents, proportionalities, of examined objects, and abnormalities and diseases associated with human tissue responsive to detected amplitudes and/or frequencies, such as resonant frequencies from the object/body being examined. Data in a database is utilized to identify the unbalanced condition, the foreign, toxic or harmful substance. The identified condition/substance may be used as an aid to select an appropriate treatment or corrective action.

23 Claims, 2 Drawing Sheets

HAND HELD

FULL ENCLOSED SCANNER

ARCH SCANNER

DETECTION AND DIAGNOSTIC SYSTEM AND METHOD

RELATED APPLICATIONS

This application is a continuation in part of U.S. application Ser. No. 11,451,227 filed Jun. 12, 2006.

FIELD OF INVENTION

The present invention relates to the detection of signals whose frequencies identify the presence of certain conditions, materials and/or elements. More specifically, the present invention relates to the detection and analysis of phenomena such resonance of elements, molecular vibrations wherein the frequencies and/or amplitudes received from objects under examination facilitate the presence of certain identifiable constituents as well as the composition, congruency, of the composition and the presence of disturbances to aid in evaluation and diagnosis of the monitored object.

BACKGROUND

It is well known in the art that certain organs have specific identifiable frequencies. For example, a liver may have a first frequency A and a heart may have a second frequency B. Harmonics of such frequencies may be examined for beneficial use, such as identifying contamination, toxicity, incongruence and dysfunction which can aid in the in-depth analysis and progress of the monitored object.

Coppleson et al. (U.S. Pat. No. 5,800,350) teaches a tissue recognition device in which a probe contacts tissue, subjecting the tissue to a plurality of different stimuli such as electrical, light, heat, sound, magnetic stimuli and detecting plural physical responses to the stimuli. These responses are transferred to a processor from a probe. The processor categorizes a tissue and then compares the categorization with a catalog of expected tissue to identify the tissue and provide an indication of tissue types such as normal, pre-cancerous/cancerous or unknown.

Lodder (U.S. Pat. No. 5,553,610) teaches the utilization of near-IR radiation and acoustic waves for the analysis of a specimen using, for example, a technique for non-invasively determining cholesterol concentrations. The non-invasive and non-destructive approach of the invention described therein can provide a diagnostic technique that may be utilized to predict the risks of stroke, confirm the existence of certain matter and even monitor the effectiveness of treatment procedures.

Brooks (U.S. Pat. No. 6,336,045) discloses a technique and apparatus for diagnosing a bone by passing a current through the bone, measuring current flow with a galvanometer and comparing stored properties with the detected property to determine the condition of the bone which information can be used for diagnostic capabilities as well as biometric recognition, the latter being similar to fingerprint and voice recognition, for example.

Schmidt (U.S. Pat. No. 6,122,537) teaches the detection of electro-magnetic signals from bodies which includes obtaining frequency components from the received signals that are characteristic of the living bodies through the use of a demodulator having a non-linear current/voltage characteristic that is frequently selective for the purpose of demodulating frequency components that are characteristics of the living bodies.

Godik (U.S. Pat. No. 6,002,958) teaches diagnosing pathological changes in tissues in a non-invasive manner through the utilization of infrared radiation together with simultaneous scanning of the investigated organ volume with the focal spot of a focus beam of amplitude modulator ultrasound waves. At least one of the parameters which appear as a result of the transmitted and/or back scattered infrared radiation is recorded and the presence and type of pathology in the investigated organ is judged by the value and/or characteristics of the relative change in parameters during the scanning process.

Dimarogonas (U.S. Pat. No. 5,836,876) teaches a method and apparatus for determining bone density and for diagnosing osteoporosis through vibrating a bone, measuring the amplitude at which the bone vibrates at given frequencies, comparing theoretical amplitudes with measured amplitudes. The invention uses standardized modal damping factors or bone density values for patients and bones having various characteristics which include age, sex, fitness level, bone type, etc. The patient's bone density or modal damping factor is then compared to the standardized values.

Wilcox (U.S. Pat. No. 6,364,849) teaches apparatus for soft tissue diagnosis by detecting responses of the soft tissue to acoustic energy. The responses to the acoustic energy are plotted for both injured and normal tissue. The comparison of the peaks indicates the presence of stress and/or injury in the soft tissue. The scan of normal tissue may be considered to be data which is stored for purposes of aiding in the analysis of damaged tissue.

Antich et al. (U.S. Pat. No. 5,038,787 likewise employs ultrasound waves for analyzing bone properties and utilizing critical angles of reflection to evaluate the mechanical properties of the material in a non-invasive manner.

It is desirable to compile information in a database which includes frequencies associated with different diseases and other characteristics of living tissue, such that it may be accessed for comparison with received frequency samples.

SUMMARY

The present invention relates to method and apparatus for detecting and identifying substances, constituents, elements, toxins, microbes, abnormalities and unbalanced conditions found in human tissue or other structures or objects based on signals sensed from the tissue (organ or body portion) or other structure. Determination of the presence of such elements, substances, toxins, microbes, unbalanced conditions or the like is based on comparison of the detected signals with related categories of stored data. The detected conditions and/or substances aid in diagnosis and, in one embodiment, aid in the selection of a proper treatment such as exposure of the monitored object with energy of a given frequency or range of frequencies and/or amplitude or range of amplitudes.

A database is created having a variety of different categories of data. For example, a category of resonant frequencies of materials such as metallic elements which may or may not be harmful to the body; a category of toxic fluids and their respective resonant frequencies; a category of resonant frequencies for healthy body organs; a category of resonant frequencies for unhealthy or diseased body organs, and the like.

Non-invasive techniques are employed to obtain readings for creating the various databases and readings are categorized according to the materials being detected and the detection devices which include, but are not limited to, electromagnetic energy sources and sensors, such as infra-red and microwave energy devices, laser sources and laser detectors, and electroluminescent sensors, sound sources and sound detectors, and other like sources and detectors/sensors capable of detecting the energy created by said sources.

The sources and detectors are provided in a variety of forms and types including hand-held devices, entire body scanners, archway scanners and the like.

Communication between and among the various components of the system may be wired, wireless and infrared, for example.

BRIEF DESCRIPTION OF THE DRAWINGS

A more detailed understanding of the invention may be had from the following description, given by way of example and to be understood in conjunction with the accompanying drawings wherein.

DETAILED DESCRIPTION OF THE PREFERRED EMBODIMENTS

Figure 1A:
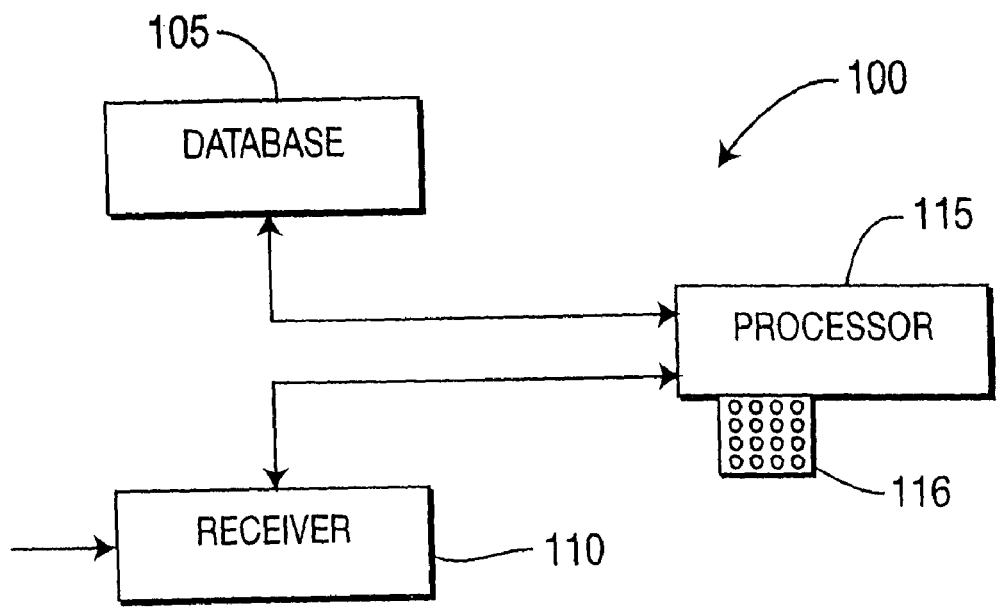
FIG. 1A is a simplified block diagram of an apparatus for developing a database in accordance with the principles of the present invention.

The preferred embodiments will be described with reference to the drawing figures where like numerals represent like elements throughout.

In accordance with several aspects of the present invention, energy emitted from an object or portion of an object being examined (such as living tissue or an inanimate body) is detected and analyzed to determine the presence of given frequencies, such as, but not limited to, resonant frequencies emitted by the monitored object and which aid in the determining the structure of the object as well as the presence of substances, components, elements, toxins, microbes and the like and to determine the if the composition of the monitored object is balanced and/or contains substances or the like which are typically not present or not present in such proportions.

The present invention may be used in conjunction with a scanning device that emits beams of energy. The scanning device may be a hand-held device shown in FIG. 2A, an enclosed full-body scanner shown in FIG. 2B or an archway scanner, such as one mounted in a doorway, shown in FIG. 2C. The present invention may be used in diagnostic medicine applications (pathology) for analyzing growth, tumors and infection (e.g., herpes virus, salmonella) associated with a human subject. Alternatively the present invention may be used for applications related to organ transplant (e.g., donor and recipient screening), airport screening, drug detection, industrial contamination detection, counterfeit money detection, presence of contraband and/or weapons which includes chemical-based weapons.

Figure 1B:
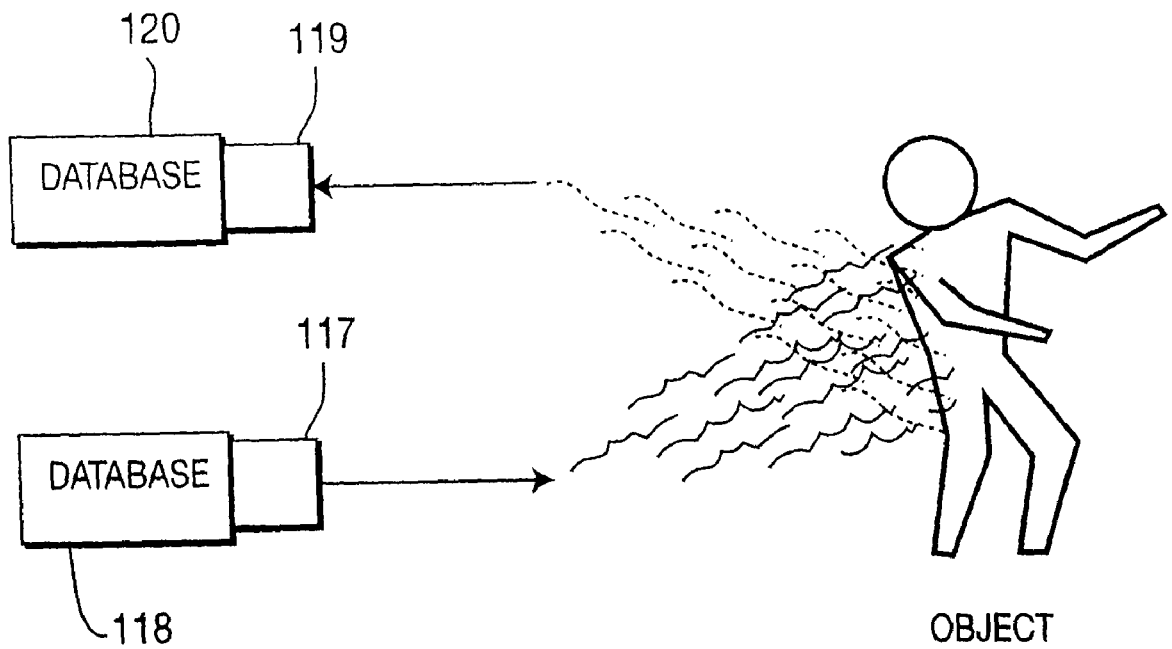
FIG. 1B is a simplified block diagram of an apparatus for obtaining and analyzing data obtained from an object being scanned or otherwise exposed to a selected energy source.

FIGS. 1A and 1B show an energy analyzer 100 and data collector operating in accordance with the present invention. Energy analyzer 100 includes a database 105, a receiver 110 and a processor 115. The database 105 stores a plurality of frequency values, such as, but not limited to, resonant frequency values unique to specific substances, toxins, microbes and other materials or sub-elements that are either inherent or which departs from a normal or balanced proportion of substances in a particular tissue, substance or other object. The data collected by receiver 110 is identified as to source by entry through an input such as a keyboard 116. Upon corroborating or ascertaining the molecular characteristics of a material, field or aura from which the molecular characteristics of various materials and storing such information in database 105, non-invasive testing may be performed on various substances, objects and structures and comparing received resonant frequency values detected by receiver 110 with correlating information stored in database 105. The comparison is implemented by processor 115. In FIG. 1B the object being examined is exposed to a selected type of energy from source 117, which may, for example, stimulate the object or portion thereof being examined. Unit 117 preferably includes the components shown in FIG. 1A (omitted from FIG. 1B for purposes of brevity). The database 118, which forms a part of energy source 117 is used to initiate a given stimuli such as a given frequency, audio, electrical, electromagnetic, infrared, or laser source and/or one or more (typically third or fourth) harmonics of the given frequency or frequencies within a given range. Sensor 119 receives energy either reflected from and/or activated by the energy from source 118 and compares it with stored data in the database (see database 105 in FIG. 1). Sensor 119 is tuned or adjusted to the range of the source frequency and further scans a wide frequency range prior to the comparison operation.

The present invention is employed to provide a database regarding the molecular state of various organs or other tissue of the body in both a healthy state and unhealthy state. Thus, once resonant (and/or other) frequency values associated with a source are analyzed, the frequency values are compared with information in the database to determine whether a specific condition exists or specific substances and the like are identified as being present in certain amounts and/or proportionalities.

The present invention calibrates impurities of molecular substances on (a) objects, (b) spaces and (c) environments, and record the frequency of emissions, and thereby aid in the selection of appropriate treatment with a view to negate and minimize degrading effects associated with the substances, impurities, unbalanced conditions or lack of congruency or harmonization detected by the monitoring activities described above.

Figure 2A:
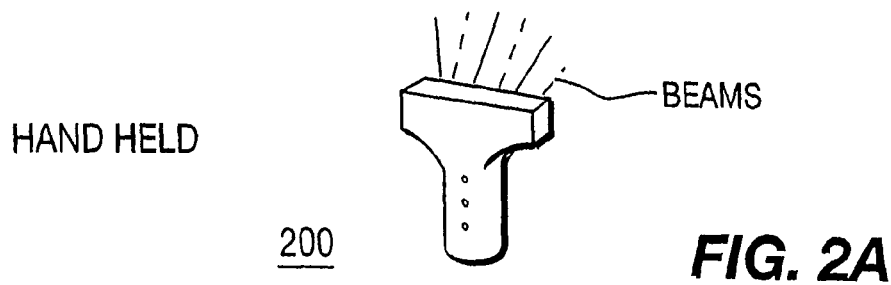
FIGS. 2A, 2B and 2C are simplified schematic views of scanners used in performing the techniques of the present invention.

The hand-held scanner 200 shown in FIG. 2A may be a laser beam generator capable of generating laser energy over a given range; an electromagnetic energy source or a sonic energy source, for example.

Figure 2B:
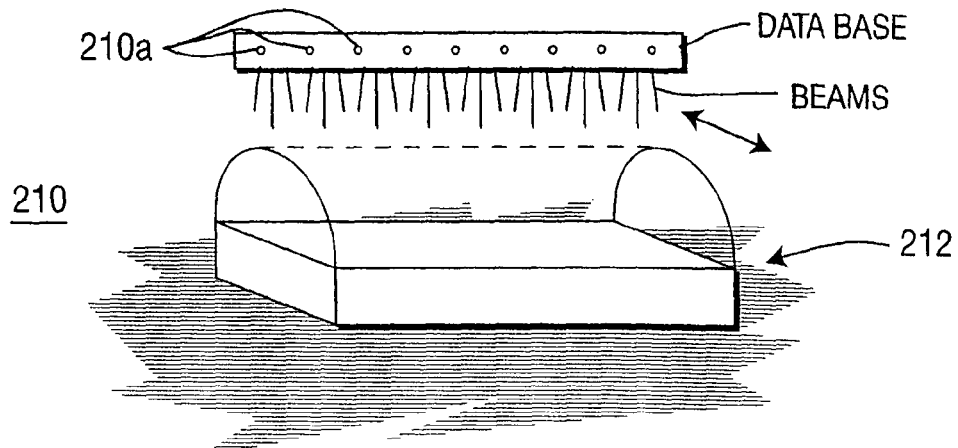
Figure 2C:
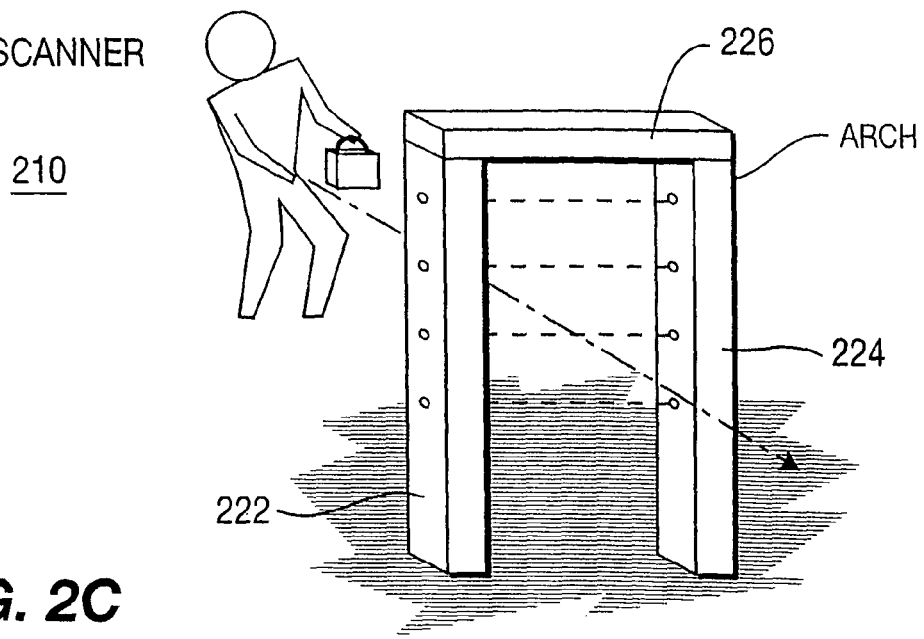

The enclosed, full-body scanner 210 shown in FIG. 2B enables scanning of the entire body or other object by means of individual scanners 210a. The scanner may sweep across the width of the support Alternatively, a single scanner may sweep across the object being scanned, for example, emitting waves either periodically or at a constant rate. The arch-type scanner 220 shown in FIG. 2C is provided with energy sources at spaced intervals about the two sides 222, 224 and top 226, conveying energy to the person walking (or object passing) through the archway or alternatively walking into (or placed in) the archway and remaining stationary for the abbreviated time required to scan the body with the energy sources.

The signals emitted by the scanning devices are reflected from the object being scanned, detected by the associated receivers and collected preparatory to processing.

In one example, a body portion or organ is scanned over a given frequency range. The energy emitted from the body portion or organ due to the energy source as a scanner is detected by the receiver which may, for example, provide a signal of varying amplitude as a function of the output frequency of the scanning energy source. These readings are converted into digital form and compared with stored data derived from the database, for example, by employing an associative memory technique.

For example, assuming that a body organ is being scanned, the identification of this organ inputted into processor 115 by way of a keyboard 116, for example. The processor accesses database 105 to obtain stored data relating to the given organ such as signals whose frequency indicate presence and proportionality of elements, substances, contaminants, microbes, toxins, or the like. The database may also be scanned for substances whose natural frequencies compare with the frequencies of signals detected by the receiver 110 associated with the particular scanner being used, such as electromagnetic wave energy operating over a wide range of frequencies, sonic energy, and light wave and infra-red wave energy.

Data relating to the given organ or other object which gives reason for concern due to lack of a balanced or harmonized state or condition due to foreign substances or toxins are also accumulated in the database, thereby enabling detection and comparison with data presently obtained by receiver 110 to determine presence of and/or changes in conditions relative to related data accessed from the database.

The scanners may also incorporate energy sources for treatment. For example, laser signals scanning the aforesaid given organ can generate both reflective and fluorescent energy from the organ. Frequencies at which fluorescence occurs, as well as the frequency value or range of the fluorescence detected. This data is analyzed to determine a laser operating frequency for treating a malignant condition.

Also, signals derived from the receiver may be analyzed to detect both normal and greater and lesser than normal levels of substances in the organ to further determine the condition of the organ.

While the present invention has been described in terms of the preferred embodiment, other variations which are within the scope of the invention as outlined in the claims below will be apparent to those skilled in the art.

What is claimed is:

1. A method of examination, comprising:
   a) providing a database having categories of data associating characteristics of electrical signals with various substances, said database further containing data relating lack of one of a balanced state or harmonized state or a condition of an organ due to substances;
   b) scanning at least a portion of a body with an energy source;
   c) detecting signals from an organ of the scanned body portion;
   d) ascertaining presence of at least one characteristic from the detected signals;
   e) comparing the characteristic ascertained with data in at least one of said data categories in said database to ascertain presence of one of said substance; and
   f) employing the database for determining a lack of one of a balanced state or harmonized state or a condition of an organ due to the detected substance.

2. The method of claim 1 wherein step (b) further comprises:
   g) exposing said body portion to a selected one of sonic, electromagnetic, infra-red, light and laser energy.

3. The method of claim 1 wherein step (g) further comprises:
   varying an amplitude of the energy source over a given range.

4. The method of claim 1 wherein step (g) further comprises:
   varying a frequency of the energy source over a given range.

5. The method of claim 1 wherein step (g) further comprises:
   varying an amplitude and a frequency of the energy source over given respective ranges.

6. The method of claim 1 further comprising:
   selecting a treatment based on said second database responsive to step (b).

7. The method of claim 1, step (c) further comprising:
   employing a sensor to detect energy from said object.

8. The method of claim 7, step (c) further comprising:
   determining a characteristic of the received energy detected by said sensor.

9. A method of examination, comprising:
   a) creating a database having categories of data associating characteristics of electrical signals with various substances, said database further containing data relating lack of one of a balanced state or harmonized state or a condition of an organ due to substances;
   b) scanning at least a portion of an object with an energy source;
   c) detecting energy from an organ of the scanned portion;
   d) ascertaining at least one characteristic of the detected signal;
   e) comparing the characteristic ascertained with data from said database to identify at least one of said substances associated with the characteristic of said detected signal; and
   f) determining a lack of one of a balanced state or harmonized state of the organ due to the detected substance.

10. The method of claim 9 wherein step (b) further comprises:
    g) exposing said portion to a selected one of sonic, electromagnetic, infra-red, light and laser energy.

11. The method of claim 9 wherein step (g) further comprises:
    varying an amplitude of the energy source over a given range during scanning.

12. The method of claim 9 wherein step (g) further comprises:
    varying a frequency of the energy source over a given range during scanning.

13. The method of claim 9 wherein step (g) further comprises:
    varying an amplitude and a frequency of the energy source over given respective ranges.

14. Examination apparatus, comprising:
    a database having categories of data associating characteristics of electrical signals with various substances and data relating lack of one of a balanced state or harmonized state or a condition of an organ due to substances;
    an energy source for scanning at least a portion of a body;
    means for detecting a signal from an organ of the scanned body portion;
    means for ascertaining presence of one of the various substances based on a comparison of at least one of the characteristics of the detected signal with the data associating characteristics of electrical signals with various substances; and
    means for comparing the characteristic ascertained with the database to determine a lack of one of a balanced state or harmonized state or a condition of an organ due to the detected substance.

15. The apparatus of claim 14, further comprising:
    said energy source providing one of sonic, electromagnetic, infra-red, light and laser energy.

16. The apparatus of claim 14, further comprising:
said energy source having means for varying an amplitude of the energy source over a given range.

17. The apparatus of claim 14, further comprising:
said energy source having means for varying a frequency of the energy source over a given range.

18. The apparatus of claim 14, further comprising:
said energy source having means for varying an amplitude and a frequency of the energy source over given respective ranges.

19. Examination apparatus, comprising:
a database having categories of data associating characteristics of electrical signals with one of various substances or elements;
an energy source for scanning at least a portion of an object;
means for detecting a signal from the scanned object portion;
means for ascertaining at least one characteristic of the detected signal;
means for comparing the characteristic ascertained with data in at least one of said data categories of said database associating the characteristic with one of the various substances and elements; and
means for determining presence of one of a substance and element in the scanned portion of the object based on said comparison.

20. The apparatus of claim 19, further comprising:
said energy source providing one of sonic, electromagnetic, infra-red, light and laser energy.

21. The apparatus of claim 19, further comprising:
said energy source having means for varying an amplitude of the energy source over a given range.

22. The apparatus of claim 19, further comprising:
said energy source having means for varying a frequency of the energy source over a given range.

23. The apparatus of claim 19, further comprising:
said energy source having means for varying an amplitude and a frequency of the energy source over given respective ranges.

* * * * *